United States Patent
Goswami

(10) Patent No.: US 9,814,866 B1
(45) Date of Patent: Nov. 14, 2017

(54) FLUSHABLE DRAINAGE DEVICE AND METHOD OF USE

(71) Applicant: Gaurav K Goswami, Fullerton, CA (US)

(72) Inventor: Gaurav K Goswami, Fullerton, CA (US)

(*) Notice: Subject to any disclaimer, the term of this patent is extended or adjusted under 35 U.S.C. 154(b) by 386 days.

(21) Appl. No.: 13/905,904

(22) Filed: May 30, 2013

Related U.S. Application Data

(60) Provisional application No. 61/653,960, filed on May 31, 2012.

(51) Int. Cl.
*A61M 27/00* (2006.01)

(52) U.S. Cl.
CPC .................. *A61M 27/00* (2013.01)

(58) Field of Classification Search
CPC ........ A61M 1/0084; A61M 27/00; A61F 5/44
USPC ............ 604/28, 31, 236, 237, 245, 247–249
See application file for complete search history.

(56) References Cited

U.S. PATENT DOCUMENTS

| | | | |
|---|---|---|---|
| 3,352,531 A | 11/1967 | Kilmarx | |
| 3,416,567 A * | 12/1968 | Tauberman | A61M 39/02 137/605 |
| 4,219,021 A * | 8/1980 | Fink | A61M 39/223 137/556.6 |
| 4,654,027 A | 3/1987 | Dragan | |
| 4,752,287 A | 6/1988 | Kurtz | |
| 5,443,453 A | 8/1995 | Walker | |
| 5,460,606 A | 10/1995 | Daneshvar | |
| 5,569,219 A | 10/1996 | Hakki | |
| 6,481,462 B2 | 11/2002 | Fillmore | |
| 6,737,000 B2 | 5/2004 | Hagel | |
| 7,302,960 B2 * | 12/2007 | Patzer | A61M 39/02 137/112 |
| 7,435,237 B2 | 10/2008 | Tan | |
| 7,717,129 B2 | 5/2010 | Steppe | |
| 7,736,339 B2 | 6/2010 | Woehr | |
| 7,842,026 B2 | 11/2010 | Cahill | |
| 2002/0000253 A1 * | 1/2002 | Fillmore | A61F 5/4405 137/607 |

FOREIGN PATENT DOCUMENTS

JP 4-212375 8/1992

* cited by examiner

*Primary Examiner* — Theodore Stigell
(74) *Attorney, Agent, or Firm* — Klein, O'Neill & Singh, LLP

(57) ABSTRACT

A flushable valve which has unidirectional flushing can be used to flush a lumen of a stent, catheter and/or tubing. By flushing the stent, catheter and/or tubing, particulates or residue that can block or impede the flow of fluid out of the stent, catheter and/or tubing can be overcome thereby facilitating continued drainage. An automatic flushable valve eliminates manual manipulation of the device. In an embodiment of the invention, a back pressure sensor can be used to detect when the flow through the stent, catheter and/or tubing has become impeded and activates a flushing cycle. In an embodiment of the invention, a leak detector can be used to detect when an operation has caused the flush device to leak. In various embodiments of the invention, the back pressure sensor and the leak detector can be used to detect that the flush device is operating under normal conditions.

19 Claims, 12 Drawing Sheets

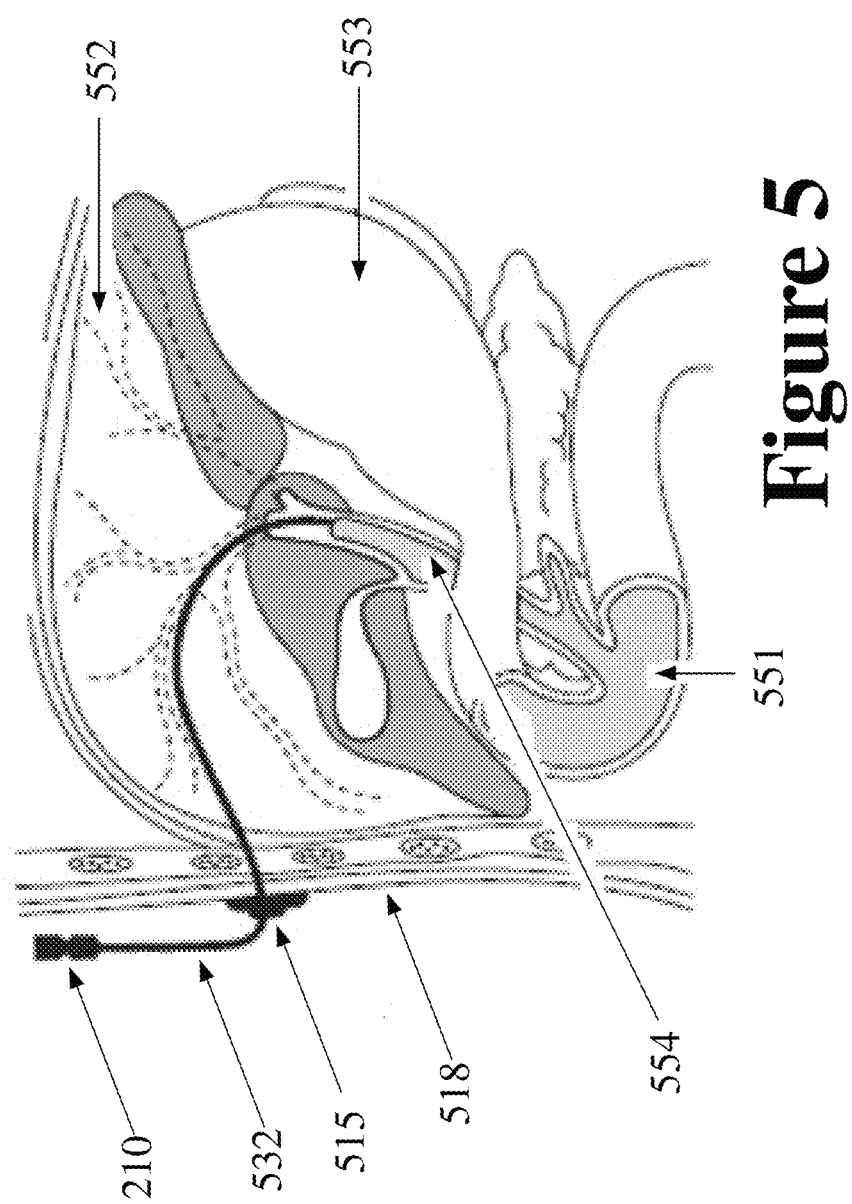

FLUSHABLE DRAINAGE DEVICE AND METHOD OF USE

PRIORITY CLAIM

This application claims priority to U.S. provisional application 61/653,960 entitled Flushable Drainage Device and Method of Use, filed May 31, 2012, inventor Gaurav K. Goswami, which is expressly incorporated by reference in its entirety.

FIELD OF THE INVENTION

The present invention relates to valves used in flushing procedures for catheters or tubes.

BACKGROUND OF THE INVENTION

In the medical field, tubes and catheters are used in a wide variety of applications including drainage procedures or applications. In these types of applications, the tubes or catheters are of the type which carry various bodily fluids, including but not limited to, abscess fluids, urinary fluids, and biliary fluids. One purpose of these tubes or catheters is to decompress, relieve, or drain a specific collection of fluid. The expressed fluid is amassed into a collection bag for evaluation or evacuation.

It is important that the interior passageway or lumen in these devices remain unobstructed from particulates and/or residues which can collect or build-up on the surface of the lumen in the catheter or tube. The build-up of particulates and/or residues on the interior surface of the lumen in the tube or catheter can lead to uneven, reduced, or obstructed flow. Obstructed, limited, or even uneven fluid flow can extend the recovery time of a patient, resulting in the potential for further complications or infections. For example, an infection can cause complications in the patient's treatment leading to sickness or even death. These problems are particularly accentuated with those catheters or tubes which are kept in place for longer periods of time.

As a result, the tubes or catheters must be periodically flushed to ensure that there is not a build-up of particulates or residue in the lumen that will block or impede the flow of fluid out of the patient. Flushing these medical devices usually involves attaching a source of cleansing fluid, such as a saline solution, and directing the cleansing fluid under low pressure through the tube or catheter to remove any build-up occurring in the lumen. The flushing fluid can then be allowed to flow out the tube or catheter into the drainage bag.

When it is time to flush the tube or catheter, the drainage bag can be disconnected and the source of cleansing fluid, usually a syringe, can be attached to the tube or catheter that is fluidly connected to the patient. Once the cleansing fluid has been directed into the tube or catheter, the syringe or other source of cleansing fluid, can be disconnected and the drainage bag can be reattached. This procedure is particularly unsatisfactory because of the time required to unscrew the drainage bag, and attach the syringe, and then to unscrew the syringe and reattach the drainage bag. In addition, after the cleansing fluid has been directed into the tube or catheter that is attached to the patient, there is a risk of fluid leaking during the un-attaching and reattaching process which can cause an unsanitary condition and potentially expose medical personnel and the patient to contamination. Further, if any fluid is accidentally discharged during this process, the medical personnel must take the time to sanitize the patient, the bedding, and themselves.

SUMMARY OF THE INVENTION

In an embodiment of the present invention, the flushing device is an intuitive unidirectional valve for regulating flow through two ports.

In an embodiment of the present invention, the flushing device allows scheduled periodic automatic flush. In an embodiment of the present invention, the flushing device undertakes a scheduled flushing of the stent, catheter and/or tubing to remove particulates that can lead to clogging of the stent, catheter and/or tubing. In various embodiments of the present invention, the flushing device undertakes the scheduled flushing of the stent, catheter and/or tubing at regular intervals. In an embodiment of the present invention, the flushing device undertakes the scheduled flushing of a filter at regular intervals. In an embodiment of the present invention, the flushing device alerts the physician and/or user when flushing fails to unclog the stent, catheter and/or tubing. In an embodiment of the present invention, the flushing device alerts the physician and/or user when flushing fails to unclog the filter. In an embodiment of the present invention, the flush device alerts personnel when the drainage receptacle requires maintenance. In an embodiment of the present invention, the flush device valve alerts personnel when there is a leak in the flush device valve system.

BRIEF DESCRIPTION OF THE DRAWINGS

This invention is described with respect to specific embodiments thereof. Additional features can be appreciated from the Figures in which:

FIG. 5 shows a schematic diagram of a flush device connecting to a stent or catheter connected to an internal organ according to an embodiment of the invention.

DETAILED DESCRIPTION OF THE INVENTION

Definitions

Figure 1A:
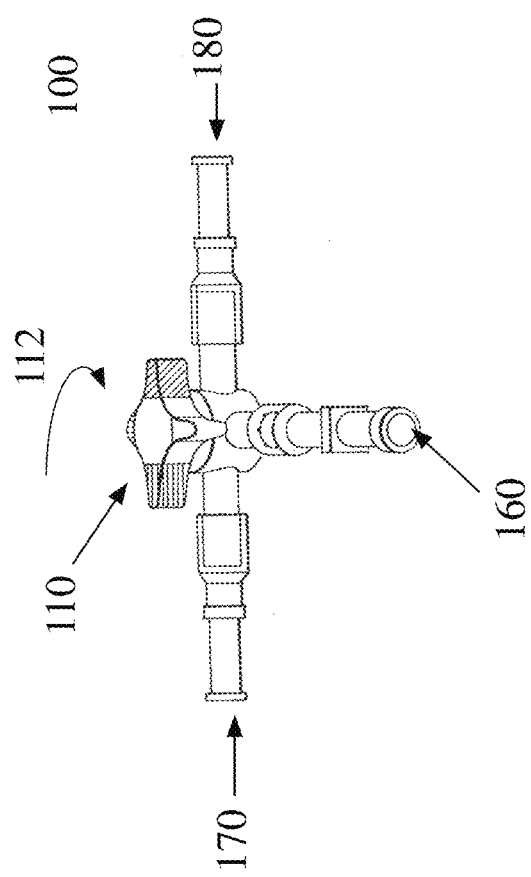
FIG. 1A shows a prior art three way stop-cock valve.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

As used herein, the term "check valve" refers to a device that has at least two openings in the body of the device, one for fluid to enter and the other for fluid to leave, and a mechanism to control the flow.

A ball check valve has a movable spherical ball part to block the flow. In some ball check valves, the ball is spring-loaded to help keep it shut. For those designs without a spring, reverse flow is required to move the ball toward the seat and create a seal. The interior surface of the main seats of ball check valves are more or less conically-tapered to guide the ball into the seat and form a positive seal when stopping reverse flow. The balls can be made of metal or other materials including artificial ruby. High pressure liquid chromatography pumps can use small drainage and inlet ball check valves with either balls and/or seats made of artificial ruby, for both hardness and chemical resistance.

A flange check valve can use a disc as a flange, rather than a ball, to block flow in a specific direction and allow flow in another direction. The flange can be circular, square, triangular or poly-sided (including a pentagon, a hexagon, a heptagon, an octagon, a nonagon, a decagon, a hendecagon, a dodecagon, a tridecagon, a tetradecagon or a pentadecagon) or some other shape. The flange can also be a combination of one or more of these shapes. Thus the flange can be mostly circular in shape but missing the area corresponding with an arc of the circle. The flange can incorporate a hinged section to retain the flange in the body of the valve while allowing the hinged portion to swing and change the direction of flow. Thus the mostly circular flange missing the arc area can be hinged along the line that intersects the extremities of the arc. A spring can be used to return the hinged section of the flange to a specific position. For example a spring can realign the hinged section of the flange on cessation of a positive pressure associated with flow of the fluid.

A mushroom check valve can use a hole with a tapered plug, such as a poppet energized by a spring.

A diaphragm check valve can use a flexing rubber diaphragm positioned to create a normally-closed valve. Pressure on the upstream side must be greater than the pressure on the downstream side by a certain amount, known as the pressure differential, for the diaphragm to open allowing flow. Once positive pressure stops, the diaphragm automatically flexes back to its original closed position.

A swing check valve or tilting disc check valve is a check valve in which the disc, the movable part to block the flow, swings on a hinge or trunnion, either onto the seat to block reverse flow or off the seat to allow forward flow. The seat opening cross-section may be perpendicular to the centerline between the two ports or at an angle.

A lift-check valve can have a disc which can be lifted up off its seat by higher pressure of drainage or upstream fluid to allow flow to the inlet or downstream side. A guide keeps motion of the disc on a vertical line, so the valve can later reseat properly. When the pressure is no longer higher, gravity or higher downstream pressure will cause the disc to lower onto its seat, shutting the valve to stop reverse flow.

A duckbill valve is a check valve in which flow proceeds through a soft tube that protrudes into the downstream side. Back-pressure collapses this tube, cutting off flow.

An electrical valve uses an electrical signal to open or close a valve. The electrical signal can drive a disc to open flow through a port.

A solenoid valve uses an electrical current through a solenoid to open or close a valve. When no electricity is applied, the valve returns to an inert position which can be used to secure the valve in a closed position in the event of an electrical failure.

A two way valve can use a check valve to direct the flow as 'on' or 'off'. A three way valve can use a check valve to direct inflow to one of two inlets.

A stop-check valve is a check valve with override control to stop flow regardless of flow direction or pressure. In addition to closing in response to backflow or insufficient positive pressure, it can also be deliberately shut by an external mechanism, thereby preventing any flow regardless of positive pressure.

Fluid level detection and fluid detection can be accomplished using a thermal resistance probe and monolithic bipolar integrated circuits such as the LM1042 Fluid Level Detector and LM1830 Fluid Detector from National Semiconductor. The fluid detector can be adjusted for the impedance of the flushing fluid.

An alarm can be a light emitting diode, a loud speaker, or a low current relay. An alarm can trigger an SMS or other message to a computer, or a cell phone or ring a pager or a cell phone.

In general, the above valves can be activated to switch from one flow configuration to a second flow configuration by application of signal either, mechanical (pressure, gears or contact) or electrical to stimulate a change in the physical configuration of the valve. Multiple check valves can be connected in series. For example, a double ball check valve in which there are two ball/seat combinations sequentially in the same body can ensure positive leak-tight shutoff when blocking reverse flow.

It is well known that fluids need to be removed from patients. Fluid removal systems typically include one or more flexible plastic tubes connecting an organ or tissue to be drained and an in-line filter connected to the one or more containers. In many instances, it is desirable to switch from one fluid container to another during patient administration either for purposes of changing the fluid being collected, or to flush the fluid delivery set-up to prevent blockage of the fluid line from occurring during use. A device commonly referred to as a three-way stopcock, can be used to flush a stent or a catheter. The three-way stopcock valve is a staple in the hospital setting for a variety of applications including the plumbing of IV tubing and catheter flushing. The device is low cost and can be reliable when used properly. The three-way stopcock valve can make it easier for medical personnel to flush a stent or a catheter and to reduce the risk of contamination and spillage. The three-way stopcock can be attached to the tube or catheter that is fluidly connected to the patient and connects the tube or catheter to the drainage bag.

The three way stop-cock valve 100 allows the passage of a bodily fluid from an inlet 180 to a drainage 170 connected to a container (not shown) and the introduction of a solution through a third port 160 to rinse the filter (not shown) (see FIG. 1A). Such valves normally employ a rotatable 112 stem 110 which allows the operator thereof to temporarily change the fluid flow from the organ communicating with the container by rotation of the stem relative to the valve (see FIG. 1B). The drainage flow 181 can be directed to the inlet 171 (see FIG. 1B(i)) or split between the inlet 171 and the third port 161 (see FIG. 1B(ii)). Similarly by rotating the stop-cock stem 110, the drainage 180 can be isolated and the inlet flushed through the third port 160 (see FIG. 1B(iii)). Alternatively, the stop-cock stem 110 can be rotated so that the inlet 170 can be isolated and the inlet 180 flushed through the third port 160 (see FIG. 1B(iv)). In this manner, a saline solution can then be directed through the three way valve into the drainage line to rinse the filter (see FIG. 1B(iv)). After removal of the saline syringe and sterilization of the three way valve, a blocking cap can be inserted on that port and by rotation of the stem relative to the valve can return the three way valve such that the fluid flow from the organ again communicates with the container (see FIG. 1B(i)).

Typically the three-way stopcock 100 has a valve that can be manually moved by the medical personnel who is going to perform the flushing procedure to direct the flow of fluid either into a drainage bag or to an outside port for periodic catheter maintenance or flushing. This allows the fluid source, such as a syringe, to be attached to the third port when it is time to flush the tube or catheter. Once the syringe is attached, the three-way stopcock can be manually moved to stop the fluid flowing to the container or drainage bag (see FIG. 1B(iv)). This allows the cleansing fluid to be directed into the tube or catheter. Once all the cleaning fluid is in the tube or catheter, the three-way stopcock can be manually moved back to its original position allowing fluid to flow into the drainage bag (see FIG. 1B(i)).

While the three-way stopcock 100 is an improvement over the manual flushing procedure, there have been various problems with the three-way stopcock 100. Stopcocks have failed from usage or have had certain limitations to their use. One of the problems with using a three-way stopcock is that the nurse or attendant must manually adjust the three-way stopcock to cease the flow of fluid in the drainage catheter and open the flushing access port to enable the flushing fluid to be directed into the lumen of the tube or catheter (see FIG. 1B(i) and FIG. 1B(iv)). One of the primary difficulties with the three way stop cock valve 100 is that it is not always apparent to the operator which position relates the fluid flow communication from the patient to the container. This is particularly true when the fluid being drained is slow moving. Two of the positions shown in FIG. 1B have no relevance (see FIG. 1B(ii) and FIG. 1B(iii)). Another common difficulty with stop-cock valves of this type is that of ensuring that the stop-cock valve remains sterile after it is placed in use, i.e., the complete sterilization of the fluid flow channels within the rotating stem thereof. Once the cleansing fluid has been directed into the tube or the catheter, the three-way stopcock must again be manually adjusted to redirect the fluid flow into the drainage bag (see FIG. 1B). These extra steps are time consuming and cumbersome requiring the attendant's and/or nurse's concentration to detail and valuable time, which are often in short supply.

Figure 1B:
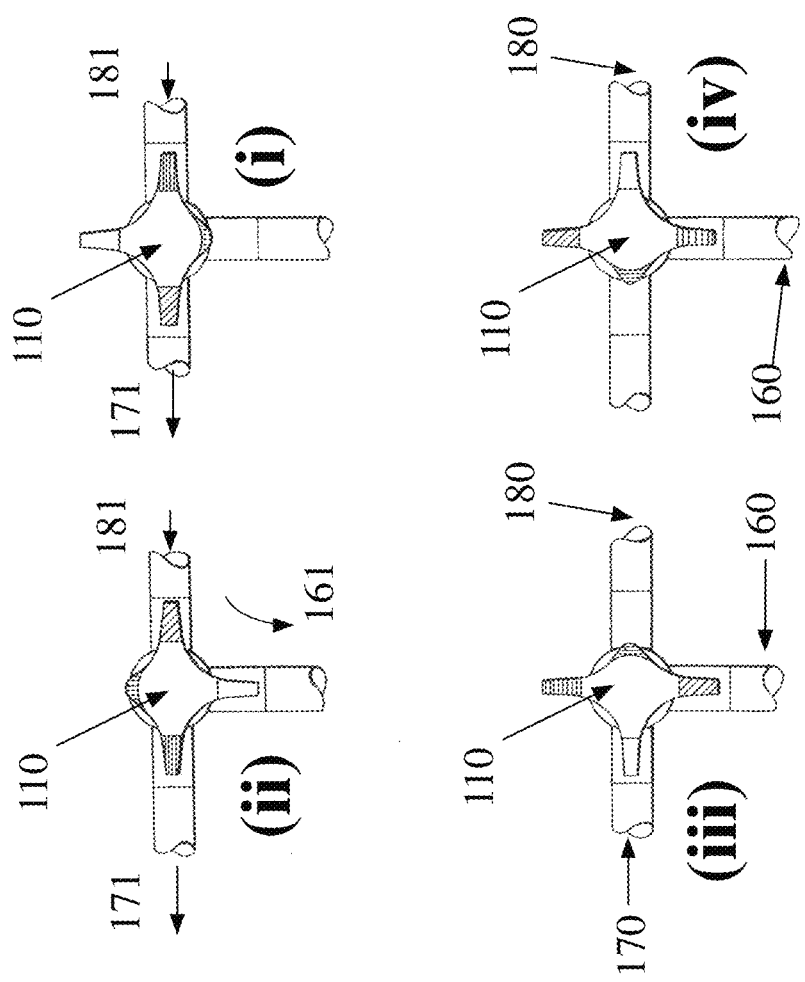
FIGS. 1B(i)-(iv) show a prior art three way stop-cock valve with the stem orientated in four (4) different directions to direct the flow.

There is also a possibility that the manual adjustments that are required can confuse the person carrying out the flushing procedure which then has the potential to misdirect the fluid flow out of the patient (see FIG. 1B(ii) and FIG. 1B(iii)). In addition, if for some reason the person fails to return the three-way stopcock to the original position which allows the fluid to flow to the drainage bag, fluid will flow out the flushing access port (see FIG. 1B(ii)) and contaminate the patient and the surrounding facilities and generally create a potentially dangerous situation. This can result in loss of fluids that are needed to monitor the health of the patient as well as creating an unsanitary condition. If the attendant fails to return the three-way stopcock from the flushing position, no drainage of the patient's fluids will ensue which can have a debilitating and even life threatening consequence for the patient (see FIG. 1B(iii)). A further problem with existing three-way stopcocks 100 is that the diameter of the passageway formed through the three-way stopcock is typically smaller than the diameter of the lumen in the tube or catheter to which the three-way stopcock 100 is attached. As a result, the passageway of the three-way stopcock 100 through the stem 110 impedes the fluid flow by creating a bottleneck effect as the fluid tries to flow through the three-way stopcock 100. The present invention addresses these problems and issues of the prior art as discussed below in detail.

Figure 2:
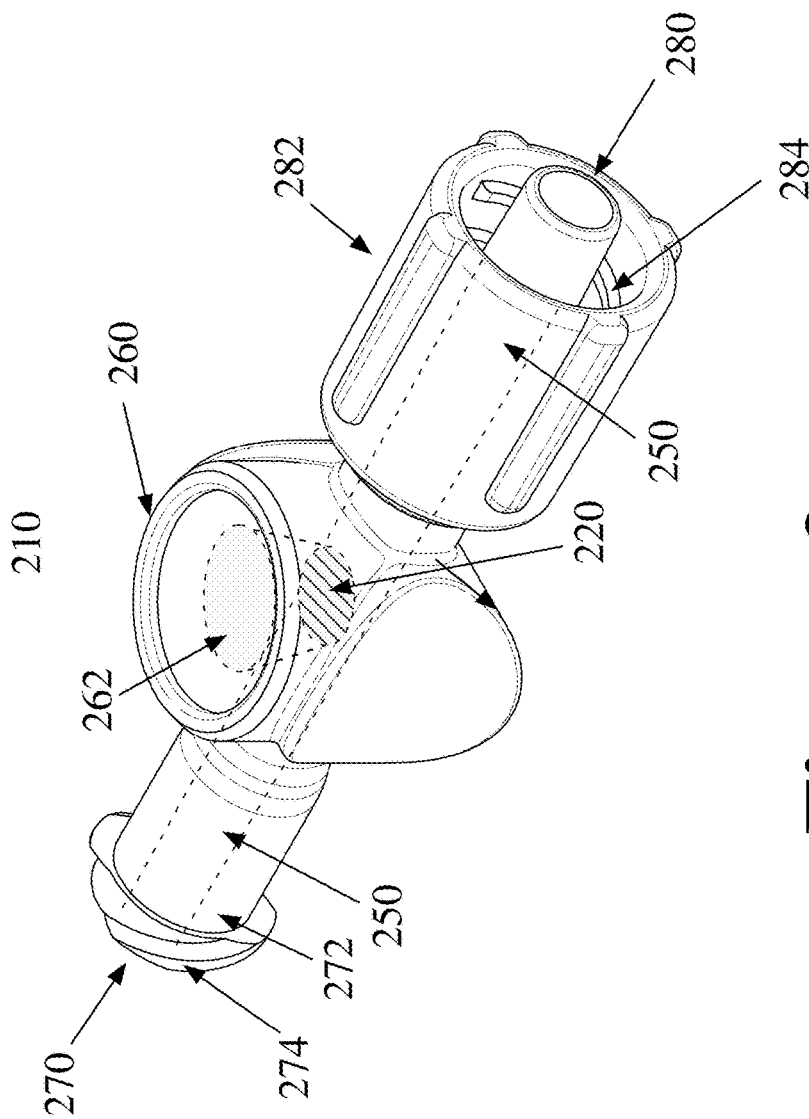
FIG. 2 shows a perspective view of a flush device according to an embodiment of the invention.

In various embodiments of the present invention, the flush device 210 can be seen in FIGS. 2-5. In FIGS. 2 and 3, the flush device 210 comprises a flange or valve plate 220, a channel 250, a flushing access channel 262, a flushing access port 260, an inlet port 280 and inlet connector 282, and a drainage port 270 and drainage connector 272 each with threaded 274 and 284 portions respectively. FIG. 2 shows a tapered flushing access port 262 suitable for a Luer lock syringe. The flange or valve plate 220 also comprises a hinge 230 (see FIGS. 3B-3E). The flush device 210 also comprises an in-line valve seat 240 (see FIG. 3B). The flange or valve plate 220 can be secured to the hinge 230 and can rotate between a first position (see FIG. 3D) and a second position (see FIG. 3E). In the first position, the flange or valve plate 220 can be located such that it does not interfere with the flow of fluid and/or materials as they move through the channel 250 from the drainage port 270 to the inlet port 280. In an embodiment, the flange or valve plate 220 can be housed in the flushing access channel 262 when in the first position. In an embodiment of the present invention, the flange or valve plate 220 can be mostly circular with an area corresponding to the area encompassed by an arc of the circle and the line connecting the extremities of the arc missing from the area of a circle or embedded into the housing 219 of the flush device 210 (See FIG. 3B). In an embodiment of the present invention, the mostly circular flange or valve plate 220 can include a hinge 230 along the straight side (corresponding to the line connecting the extremities of the arc). In an embodiment of the present invention, the mostly circular flange or valve plate 220 can include a spring (not shown) to return the mostly circular portion of the flange or valve plate 220 to a set return position (see FIG. 4C). In an embodiment of the present invention, the absence of positive pressure at the flange or valve plate 220 would move back to the return position. In an embodiment of the present invention, attaching a pump or syringe 405 to the flushing port 260 moves a lever (not shown) which displaces the flange or valve plate 220 connecting the flushing port 260 and the inlet port 280. Removal of the pump or syringe 405 connection from the flushing port 260 moves the flange or valve plate 220 back to the return position. In an embodiment of the present invention, the center of the flange or valve plate 220 can be off center to the center of the channel 250. In an embodiment of the invention, despite the offset of the flange or valve plate 220 relative to the center of the channel 250, the flange or valve plate 220 can seal on the valve seat 240.

Figure 3A:
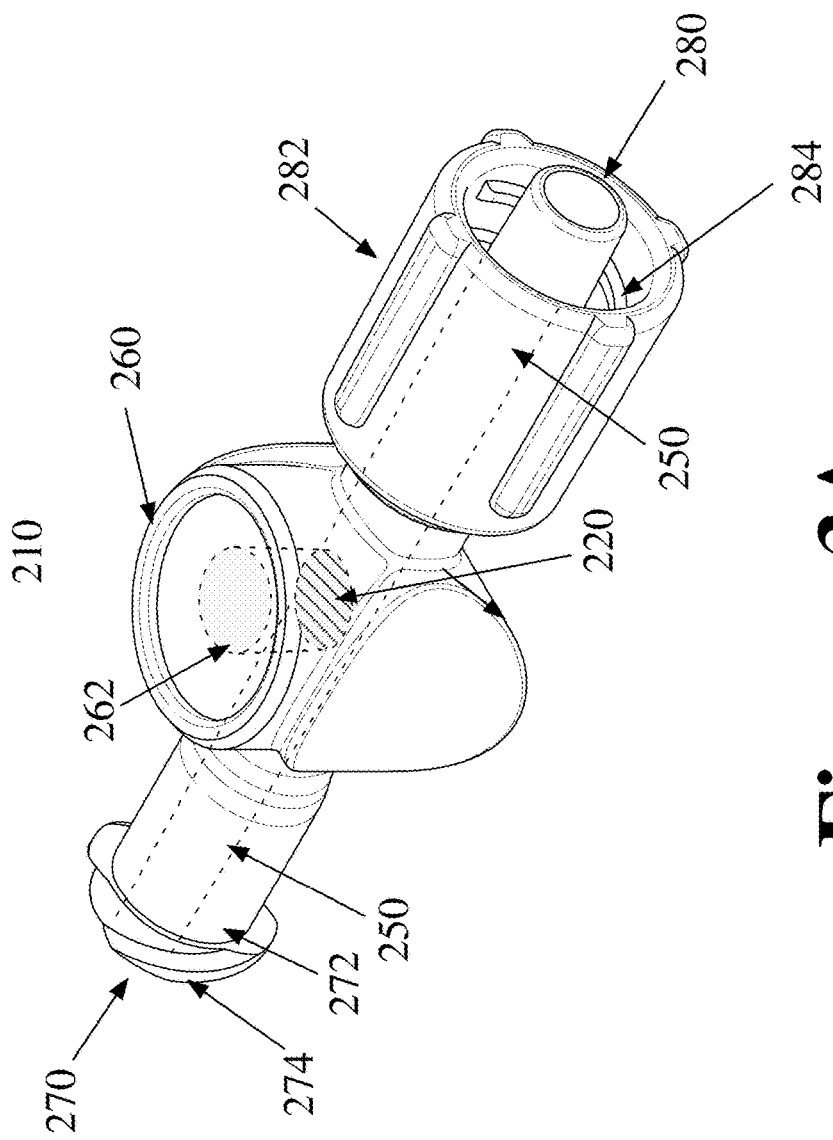
FIG. 3A shows a perspective view of a flush device according to an embodiment of the invention.
Figure 3B:
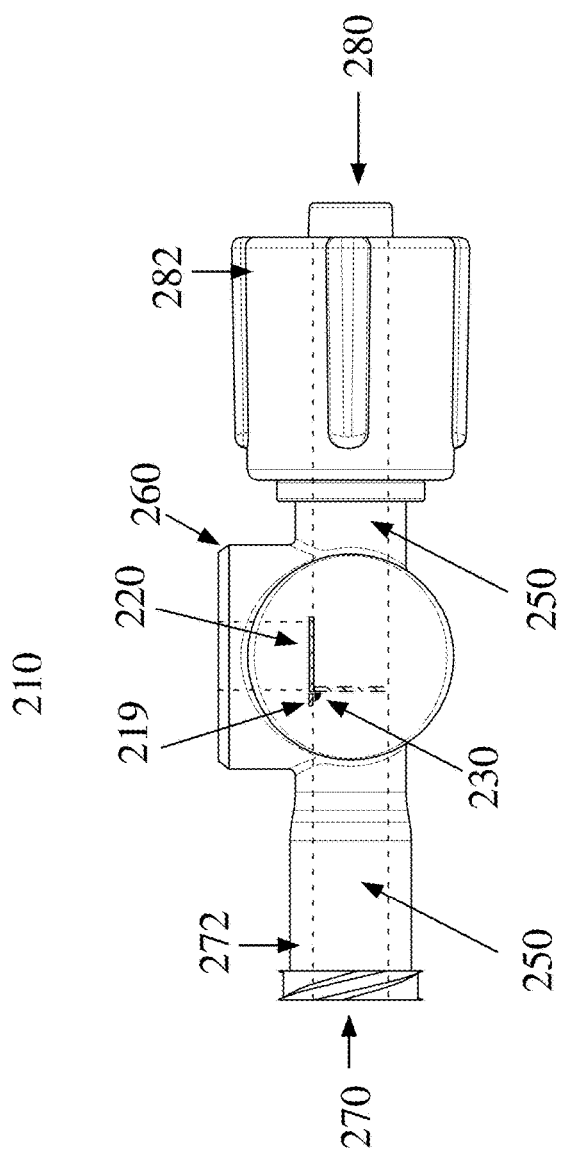
FIG. 3B shows a side view of a flush device in the 'drain' configuration and the direction of movement of the flange or valve plate from the 'flush' configuration according to an embodiment of the invention.
Figure 3C:
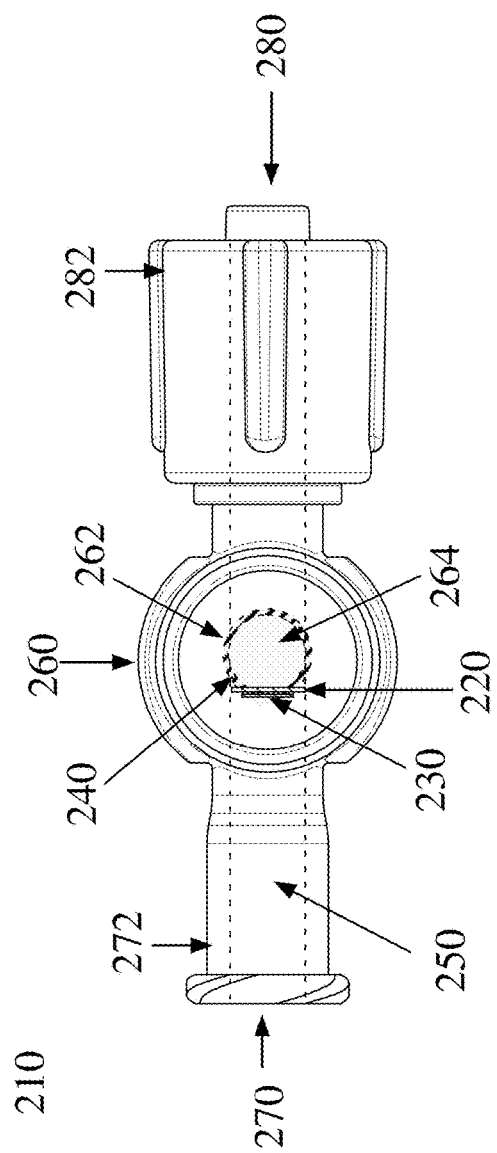
FIG. 3C shows an overhead view of a flush device according to an embodiment of the invention.
Figure 3D:
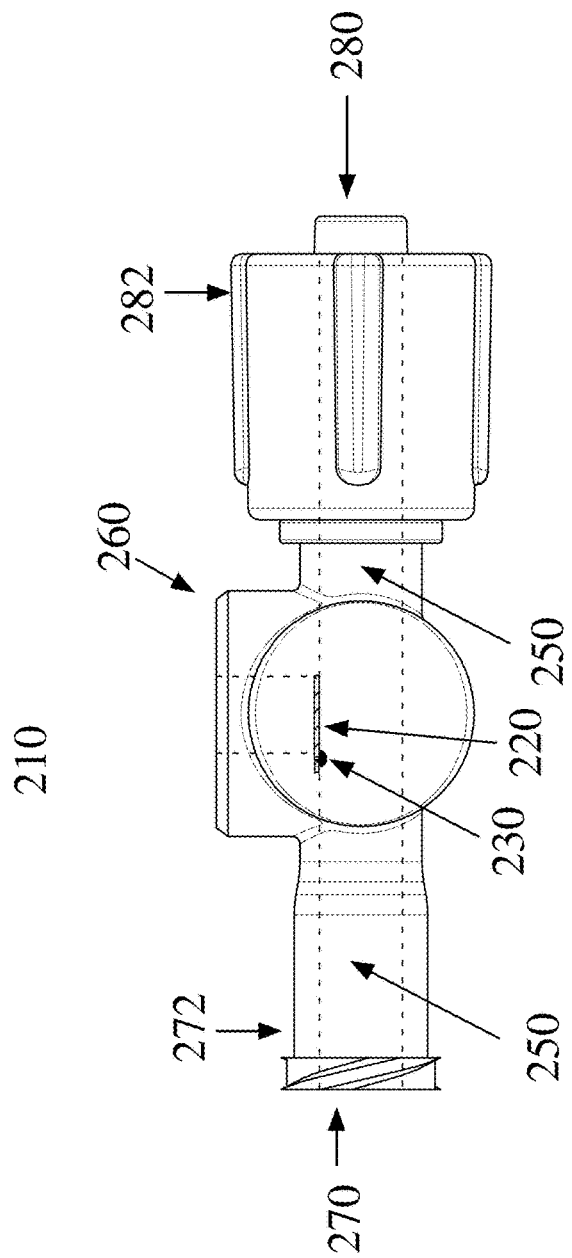
FIG. 3D shows a side view of a flush device in the 'drain' configuration according to an embodiment of the invention.
Figure 3E:
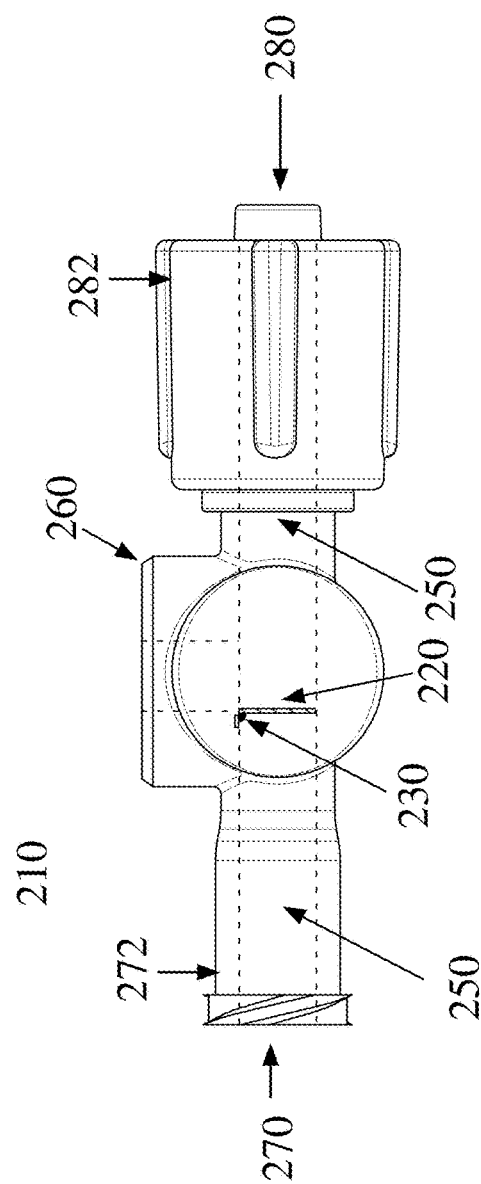
FIG. 3E shows a side view of a flush device in the 'flush' configuration according to an embodiment of the invention.
Figure 4A:
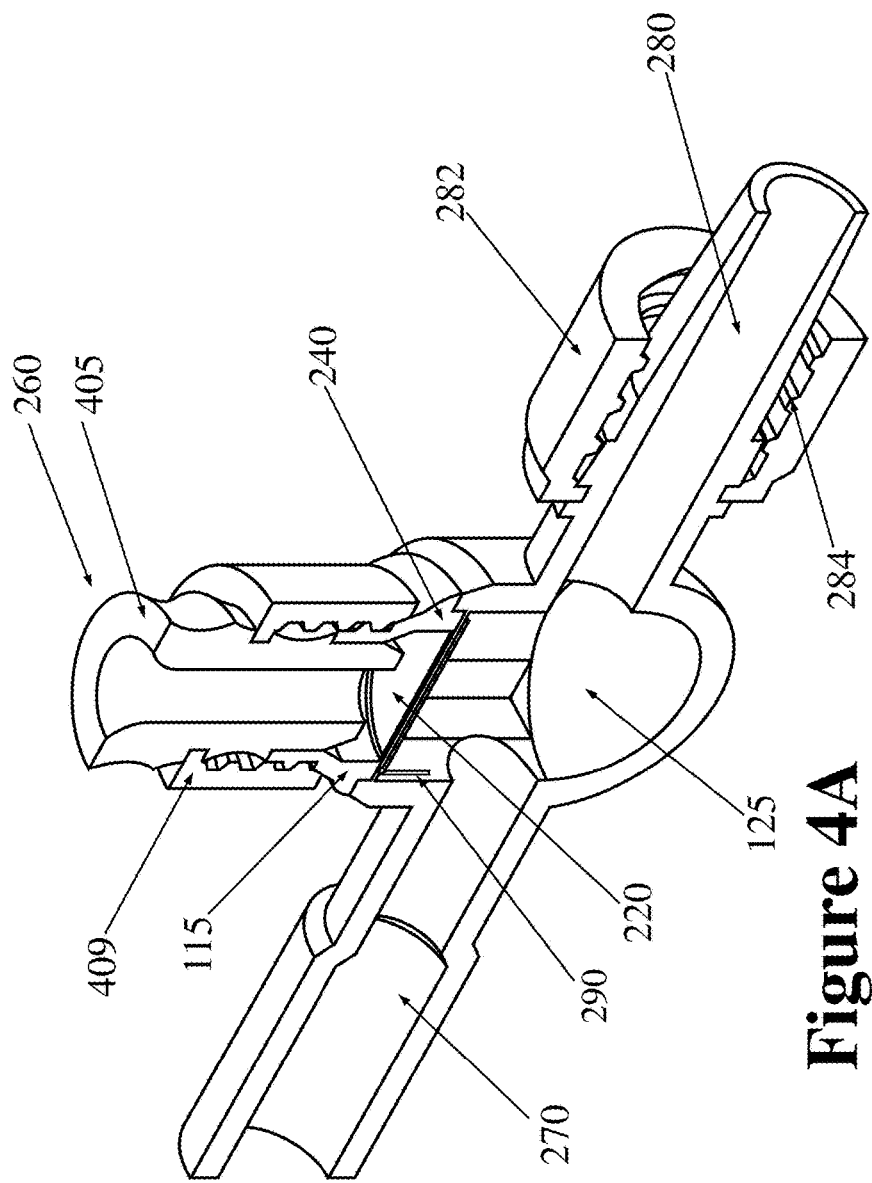
FIG. 4A shows a section schematic of a flush device system in the 'drain' configuration according to an embodiment of the invention.
Figure 4B:
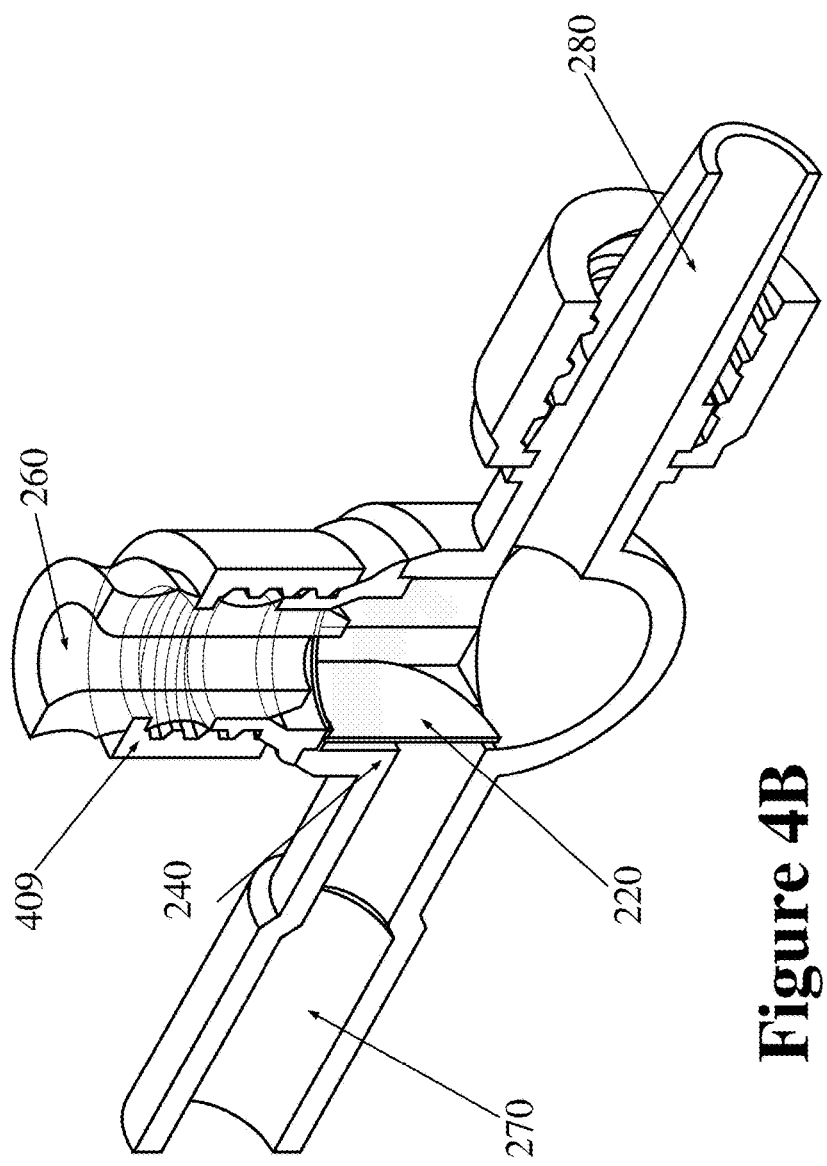
FIG. 4B shows a section schematic of a flush device system in the 'flush' configuration according to an embodiment of the invention.
Figure 4C:
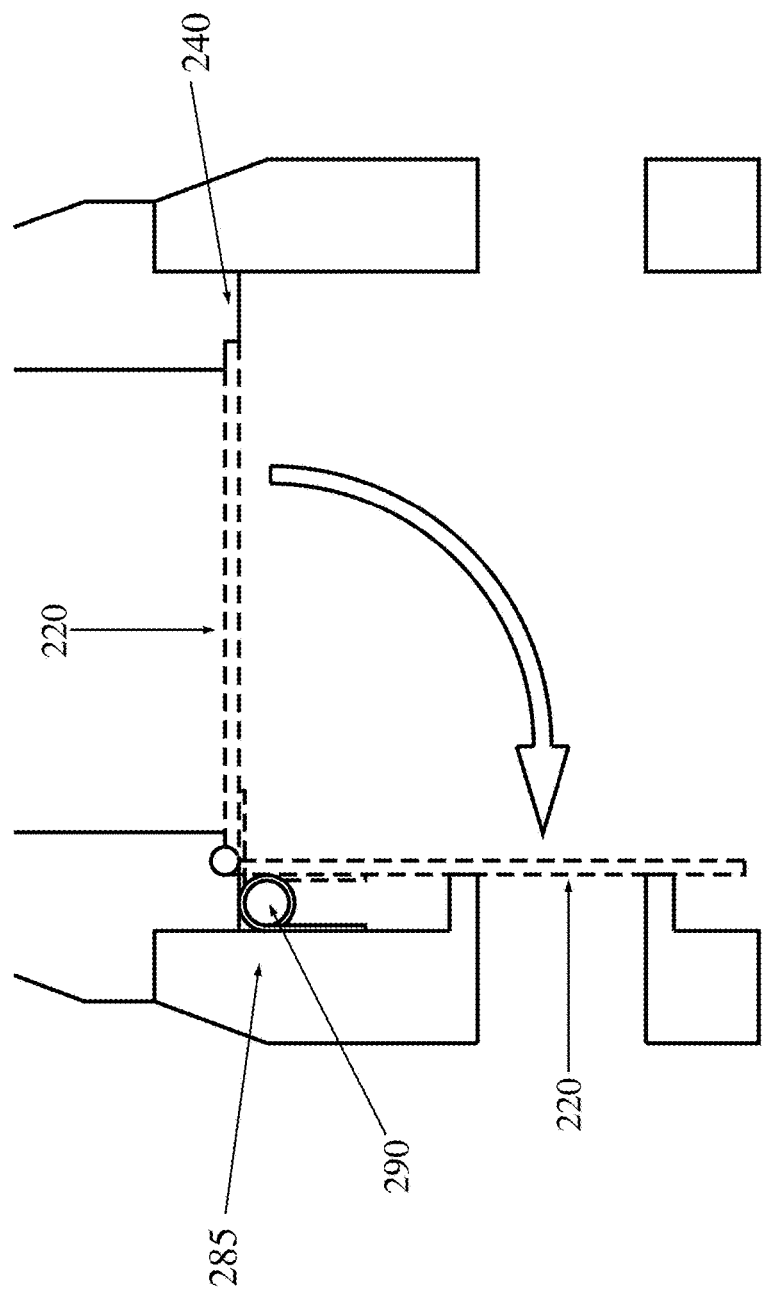
FIG. 4C shows the movement of the flange or valve plate relative to a section schematic of a flush device system according to an embodiment of the invention.

In an embodiment of the present invention shown in FIG. 3A-FIG. 3E, FIG. 4A-FIG. 4B and FIG. 5A-FIG. 5B, the automatic flush device 210 has a flange or valve plate 220 that moves in response to the fluid pressure applied by the action of a flush fluid being introduced into the flush device 210 via the flushing access port 260. The flange or valve plate 220 moves from a first position (see FIG. 3D; FIG. 4A; FIG. 5A) to a second position (see FIG. 3E; FIG. 4B; FIG. 5B), wherein the flange or valve plate 220 abuts the in-line valve seat 240. When moving from the first position to the second position, the flange or valve plate 220 rotates about a hinge 230. In the second position, the valve plate 220 substantially prevents flush fluid from flowing into the drainage port 270 and directs the flush fluid into the inlet port 280. Thus, the flush fluid, and pressure thereof, can be directed out of the inlet port 280 entrance passage way and towards any occlusion in the attached pathway. As shown in FIG. 4A-FIG. 4C, a syringe head 405 can be screwed into the thread 409 of the flushing access port 262. The flange or valve plate 220 can seal on the valve seat 240. Similarly, the tubing connecting the catheter or stent via the inlet port 280 to the flush device 210 and the tubing connecting the flush device 210 to the drain bag can be connected to the flush device 210 by threading to the thread 272 of a screw fit connector.

In an embodiment of the present invention shown in FIG. 2 and FIG. 3A the flushing access channel 262 comprises a flushing access port 260. In FIG. 2A, the flushing access port 260 is configured to receive a tip of a syringe (not shown). In various embodiments of the present invention, the filter comprises a connector (not shown). The connector can be a female Luer lock fitting that is capable of accepting a male Luer lock tipped syringe. In various other embodiments of the present invention, while the flushing access port 260 can accept a syringe having a male Luer lock tip, the access connector will not have a female Luer lock fitting. The center part of the syringe's male Luer lock fitting can be inserted through the flushing access port 260, and the fluid therein can be introduced into the flush device 210.

In an embodiment of the present invention, the flushing access channel 262 can further define an access valve (not shown). The additional access valve can serve to prevent contamination of the system and spillage of the fluids contained therein.

In various embodiments of the present invention, when the valve plate 220 is in the first position, it is received within the flushing access channel 262. Additionally, the valve plate 220 can abut the access valve seat 240. When the syringe is inserted and the flush fluid introduced, the pressure of the flush fluid can unseat the valve plate 220 from the access valve seat 240 and move the valve plate 220 to the second position. The seal created by the valve plate 220 and the access valve seat 240 can serve as the access valve. In addition, the seal created by the valve plate 220 and the access valve seat 240 can serve in conjunction with the spring 290 to act as the access valve. Additionally, the seal created by the valve plate 220 and the access valve seat 240 can serve in conjunction with an additional valve to act as the access valve. This arrangement can provide further protection from spillage and/or contamination.

In an embodiment of the present invention, the drainage port 270 can have a drainage connector 272. In some embodiments, the connector is a conventional male Luer lock fitting (not shown). There can also be a threaded portion 274 that can accept a corresponding male threaded portion (not shown). Other conventional fittings can be used as well. Other embodiments of the drainage connector 272 can be a female Luer lock fitting with threaded portion (not shown) into which a male Luer lock fitting can be inserted (not shown).

In an embodiment of the present invention, the inlet port 280 can have an inlet connector 282. In various embodiments of the present invention, the connector is a conventional female Luer lock fitting 282 with threaded portion 284 (see FIG. 2). A male Luer lock fitting (not shown) can be inserted and rotate about the female Luer lock fitting 282. The male Luer lock fitting can have threaded portion (not shown) that can accept the corresponding threaded portion 284 of the female Luer lock fitting 282. Other conventional fittings can be used as well. Other embodiments of the inlet connector 282 include a male Luer lock fitting (not shown) and the threaded portion (not shown) that accepts a corresponding female threaded portion (not shown).

In an embodiment of the present invention, the in-line valve seat 240 can be located where the channel 250 and the inlet portion meet. The shape of the in-line valve seat 240 can be such that it can form a seal with the valve plate 220 when it is in the second position. The profile of the in-line valve seat 240 can be vertical or diagonal. If the profile of the in-line valve seat 240 is diagonal, this can limit the range of movement required by the valve plate 220 to actuate from the first position to the second position.

In an embodiment of the present invention, the inline valve seat can also either be a projection or a ledge defined by the channel 250 and wall of the inlet conduit.

In various embodiments of the present invention, the valve plate 220 can have a variety of outlines. The outline can be round, rounded with a linear side, square, and triangular. The cross-section of the valve plate 220 can have an angled lower end, vary in thickness, be linear, be concave, and/or be convex. The concaved cross-section can help increase the pressure applied against the in-line valve seat in the second position. Additionally, the angled lower end can help prevent the valve plate from catching on particulate and help force the valve plate 220 into the first position as matter flows through the channel. The angled lower end can span the entire portion of the valve plate 220 and can extend along the entire exposed periphery of the valve plate (e.g. the part that is not attached to the hinge), the leading edge of the valve plate that encounters the downstream flow, or any portion thereof. It is also understood that valve plate 220 can have appropriate accommodation in the first position so that it will not impede flow.

In an embodiment of the present invention, a spring 290 biases the valve plate 220 toward the first position (see FIG. 4A and FIG. 4C). In an embodiment of the invention, the spring 290 is a tension spring. In an alternative embodiment of the invention, the spring 290 is a compression spring. In another embodiment of the invention, the spring 290 is a wire torsion spring. In a further embodiment of the invention, the spring 290 is a double wire torsion spring with an offset. In another embodiment of the invention, one of the hook ends of the wire torsion spring 290 can be embedded in the body 285 of the flush device 210. In another embodiment of the invention, one of the hook ends of the wire torsion spring 290 can be embedded in the body of the valve plate 220.

In an embodiment of the present invention, the inlet port 280, channel 250, flushing access channel 262, drainage port 270, or any combination thereof is made of a translucent material that can allow a person to see the valve plate 220 in at least the second position. The valve plate can have a colour that makes it easier to see. In other embodiments the valve plate 220 can have a coloured dot or other marking that can be seen through the translucent body by the flush device operator.

As mentioned above, in some embodiments, the valve plate 220 of the flushing access port 260 can form a seal in the first position with the access valve seat 240. In other embodiments that valve plate 220 can have a projection that can correspond with the access orifice 264 (see FIG. 3C); such that when the valve plate 220 is in the first position, the projection can reside in the access orifice. The access orifice 264 can serve as the access valve seat 240 or as an additional valve seat. In one embodiment the projection is round and the flushing access channel defines a stepped cross-section that can accommodate the valve plate 220 and the projection when the valve plate 220 is in the first position.

In an embodiment of the invention, the flush device includes an external leak detector. In an embodiment of the invention, detection of leaking serum activates one or more functions selected from the group consisting of activate an alarm; terminate a flushing operation; raise an alarm and initiate a flushing operation sequence to reseat the flange and raise an alarm and an auto shut-off sequence.

In an embodiment of the present invention, wireless communications circuitry can provide modulated waveform signals in either the infrared (IR) or radio frequency (RF) signal range. In an embodiment of the invention, the wireless communications circuitry can provide RF inputs/outputs. The modulated signals can be transmitted using any typical small computer Ethernet system WiFi standard such as EIA-802.11G, Bluetooth® methodology or discrete signalling utilizing a non-linear code encryption algorithm for secure control. The wireless communications circuitry can be controlled through an interface with the device processor circuitry to provide remote control and data transfer between the flush device 210 and peripheral devices such as: remote control units (pushbuttons, foot switches), devices for monitoring the content of the drainage bag, devices for monitoring the leakage of fluid from the flush device 210, personal computers, printers or other portable computing devices such as personal digital assistants (PDA), mass storage devices, or digital telecom devices such as cellular telephones.

In an embodiment of the present invention, device processor circuitry can be comprised of typical microprocessor electronic components necessary to provide pre-programmed and user-selected operation of the flush device 210. In various embodiments of the present invention, components of the processor circuitry include but are not limited to: volatile and non-volatile memory, real-time clocking, and peripheral interface and logic devices. In an embodiment of the present invention, a sensor can monitor the back pressure of the flush device 210 and alert the attendant of the need to flush a stent, a catheter, tubing and/or a filter. In an alternative embodiment of the present invention, a sensor can monitor the back pressure of the flush device 210 and carry out a periodic flushing of a stent, a catheter, tubing and/or a filter. Based on the back pressure during the periodic flushing the processor can be programmed to determine that (i) there is no impediment of the stent, the catheter, tubing and/or the filter and return the flush device 210 to drainage until the next periodic check, (ii) there is an impediment to the stent, catheter, tubing and/or filter and undertake an extended flushing until the impediment is removed and then return the flush device 210 to drainage until the next periodic check, or (iii) there is an impediment that is not removed by flushing that requires intervention and then return the flush device 210 for limited drainage and alert for intervention. In an embodiment of the present invention, the flush device 210 alerts the physician and/or user when flushing fails to unclog the stent, catheter, tubing and/or filter. In an embodiment of the present invention, the system monitors the volume of liquid in the drainage receptacle or bag and alerts personnel when the drainage receptacle or bag requires maintenance. In an embodiment of the present invention, the system monitors for leaks in the flush device 210 and alerts personnel when there is a leak in the system. In an embodiment of the invention, monitoring for leaks can include chemical/biological detection of the leaking fluid. In an embodiment of the invention, monitoring for leaks can be based on differentiating flushing fluid from biological fluid using atmospheric ionization and spectroscopic analysis to analyse for chemical or biological markers present in the biological fluid but not present in the flushing fluid. In an embodiment of the invention, monitoring for leaks with atmospheric ionization can utilize the direct analysis real time (DART) technique as outlined in U.S. Pat. Nos. RE43,078, 7,700,913 and 7,777,181 entitled "ATMOSPHERIC PRESSURE ION SOURCE"; "SAMPLING SYSTEM FOR USE WITH SURFACE IONIZATION SPECTROSCOPY" and "HIGH RESOLUTION SAMPLING SYSTEM FOR USE WITH SURFACE IONIZATION TECHNOLOGY" which are herein expressly incorporated by reference in their entireties. In an embodiment of the present invention, an internal system processor firmware program can provide the direction to operate the various circuit blocks that reside on the device circuit board. Functionality provided by the firmware can include:

a) comparison of desired and actual back pressure through the filter and flush device 210. In an embodiment of the present invention, a control algorithm can be used to control hysteresis and thereby minimize or eliminate oscillatory cycling of the back pressure alert;

b) activation of the back pressure valve to control the flushing device to flush the stent, catheter, tubing and/or filter and maintain the user-selected back pressure;

c) logic output signal control to effect a proportional indication of the back pressure sensor signal at an LED bar graph indicator;

d) interface logic for the operator display and controls to provide user adjustments of the flush device 210 and to provide status messaging and data during operation;

e) control of the wireless communication circuitry to implement the properly formatted exchange of data with other peripheral devices; and f) control of the external memory and interface port to provide the proper transfer of stored histogram data to external memory storage devices, and the bi-directional communication required to effect remote control of the flush device 210 using an external host computing device.

In an embodiment of the present invention, the flushing device can be a miniature pump utilizing any typical pressure building chamber-type mechanism such as diaphragm, bellows or piston. In an embodiment of the present invention, an energy storage device can provide power to a device circuit board to control the flushing device.

In an embodiment of the present invention, the flushing device can include flexible tubing to deliver a filtered solution to the flushing device. The flexible tubing can be of surgical quality manufactured of any typical material such as PVC, rubber (natural or synthetic), silicone or others. The flexible tubing can be sized to provide an airtight connection between the pump, the flush device 210.

In an embodiment of the present invention, a wireless control unit can be a small form factor self-contained RF transmitter with an integral storage battery power source. In an embodiment of the present invention, the wireless control unit can be wirelessly connected to the flush device 210 utilizing the wireless communications circuitry with discrete signalling utilizing a non-linear code encryption algorithm for secure control. The wireless control unit can allow the flush device 210 to be operated remotely. Through the actuation of a single or predefined combination of buttons, the operation of the flush device 210 can be controlled. Control functions include: pump on/off, switching of flow of flush device 210 from drainage to flush, flushing of the filter, flush time duration, switching of flow from flush to drainage and adjustment of other operating parameters as afforded by the device processor circuitry.

The check valve can be an in-line, 2-port miniature fluid valve utilizing swing disk diaphragm, ball, or other seating methods typical in the art. The check valve allows fluid flow in only one direction, away from the pump. Disk or ball check valves can be free moving or utilize levers or springs to assist in seating faster to eliminate fluid flow shock and/or inhibit fluid flow based upon applied pressure. The check valve can be positioned to eliminate fluid leakage through the pump when the pump is not operating.

The flush device is initially in an 'off' state, with no power applied to the internal components. Prior to operation, the physician attaches the catheter 532 through an incision 515 in the epithelial tissue 518 to the stomach 553 or liver 552 to be drained via the common bile duct 554 of the duodenum 551 and connects the flush device to the catheter 532 and a drainage bag (not shown) to the drainage port (not shown) of the flush device (see FIG. 5). A syringe or pump (not shown) with a saline solution is connected to the flushing port of the flush device (not shown). Then the user applies positive pressure via the syringe or pump to the flush device and positions the selector switch to the desired operating back pressure.

The device processor circuitry determines if the pump is required to operate, or not, based upon the relationship between the user setting of the selector switch and the signal magnitude of the back pressure sensor and the time elapsed. Once activated the flush device begins to monitor and store the data including switching the flush device from drainage to flush and flushing to carry out a periodic check of the stent, catheter, tubing and/or filter back pressure and thereby monitor at regular intervals. If the back pressure sensor is lower than the desired reading there is no impediment in the filter (i.e., the filter is not clogged or at risk of being clogged) as determined by the signal from the back pressure sensor and the flush device is switched from flush to drainage. However, if the back pressure sensor indicates a higher reading than the desired level then the solution is passed through the stent, catheter, tubing and/or filter until either the back pressure reading falls below a prescribed level or a duration of flushing time elapses. In the situation when the time duration for flushing has elapsed and the back pressure has not fallen below the prescribed level an alarm may begin to indicate that the filter is blocked. The relative back pressure sensor reading is given by the LED bar graph indicator, with the value of the back pressure sensor signal proportionately indicated by sequential LED indicator illumination from the bottom of the bar graph to the top.

During the operation of the flush device, back pressure data can be stored in non-volatile memory that forms a part of the device processor circuitry. The back pressure data can be stored sequentially with associated real-time (time of day) values that provide a direct correlation of the operating back pressure at a given time. The stored memory data can be retrieved by the user. In various embodiments of the invention, the stored memory data can be retrieved by: (a) negotiation and data download to an external device using the wireless communication circuitry, (b) insertion of a non-volatile memory device (flash/thumb drive) at the external memory and interface port; or (c) by request (serial communication) of a host computer connected to the external memory and interface port.

With the operator display and controls, the user may perform various functions that affect the operation of the flush device; these functions include, but are not limited to:

(i) adjust dead-band (+/−error range of back pressure signal when compared to desired background back pressure) and delay time before/after allowable error is exceeded to activate/de-activate flush pump settings or parameters;

(ii) adjust preset back pressure values associated with the user back pressure selector switch;

(iii) monitor back pressure in real-time with display provided in selectable engineering units including mm/Hg, bar, mbar, torr, mtorr, PSI and kPa;

(iv) retrieve and view stored time-stamped back pressure histogram values; and (v) adjust other system parameters associated with the functionality of the LED bar graph indicator and communication protocols used by the external memory and interface port and the wireless communication circuitry.

In an embodiment of the present invention, the back pressure selector switch can be expanded in functionality to include: more selections (positions) and factory pre-set operational values. In an alternative embodiment of the present invention, the back pressure selector switch can be eliminated completely and replaced by a single pre-set or adjustable setting through the use of the operator display and controls. In another embodiment of the present invention, the back pressure selector switch can be set according to the procedure being undertaken. In an embodiment of the present invention, the minimum and maximum pressure which can be selected during the procedure can be based on the procedure being undertaken. In an embodiment of the present invention, the minimum and maximum pressure which can be selected can be based on the stored identity of a physician carrying out the procedure. The identity of the physician carrying out the procedure can be detected through a RFID reader associated with the flush device and a tag associated with the physician. In an embodiment of the present invention, the minimum and maximum pressure which can be selected during the procedure can be restricted based on the procedure being undertaken.

The functionality of the LED bar graph indicator can be expanded to allow user selected indications that provide: 0-100% indication of the back pressure sensor signal, scaled to provide 0-100% indication of the back pressure selector switch pre-set range, or other user selected range of indication.

In an embodiment of the present invention, the flush device can be reconfigured to utilize simple electronic circuit components eliminating the need for the device processor circuitry.

In various embodiment of the present invention, the unique operational characteristics of the flush device can be utilized with pumps of any size or type by modifying the pump control circuitry and the back pressure sensor expanding the size and types of back pressure assisted devices that can be supported.

In an embodiment of the present invention, the back pressure records can be stored in the processor memory during the execution of the medical procedure. In an embodiment of the present invention, upon the conclusion of the procedure, the back pressure records, stored in the processor memory during the execution of the procedure can be retrieved. In an embodiment of the invention, the back pressure records can be in the form of a histogram. The retrieval of the stored data can be performed by the simple insertion of a flash memory device into the external memory and interface port or by connection of this port to a host computer for subsequent download. Once the medical procedure is completed, and/or the stored data is retrieved, the flush device can then be powered off using the power switch.

In an embodiment of the invention, the system control functionality of the flush device can be used to provide fluid delivery, through the simple exchange of pump hose connectivity, sensor selection and processor firmware control algorithm changes.

In another embodiment of the invention, a Radio Frequency IDentification (RFID) tag is imbedded in one or more of: the flush devices. In an embodiment of the invention, the RFID tag is used to identify the flush device and thereby determine the parameters for operation of the flush device. In one embodiment of the invention, the RFID tag operates using an Ultra High Frequency (UHF) signal. In another embodiment of the invention, the RFID tag operates using a microwave frequency signal.

In an embodiment of the present invention, a RFID reader is present in the flush device which can then read the RFID tags in the individual filter. In an embodiment of the invention, the RFID reader can be positioned so that the RFID tag antenna is least affected by any conducting material. In an embodiment of the present invention, a microcontroller interfaces with an embedded RFID read/write module to write to a programmable RFID tag.

In one embodiment the RFID tag is read only. In another embodiment, the RFID tag contains an Electrically Erasable Programmable Read-Only Memory (EPROM), which enables both read and write functions. In an embodiment of the invention, the RFID tag is passive. In another embodiment of the invention, the RFID tag is semi-passive containing a source of energy such as a battery to allow the tag to be constantly powered. In a further embodiment of the invention, the RFID tag is active, containing an internal power source, such as a battery, which is used to power any Integrated Circuits (ICs) in the tag and generate the outgoing signal. In another embodiment, the tag has the ability to enable location sensing through a photo sensor.

In an embodiment of the invention, the flush device is able to monitor the type, previous use data and condition of the filter. In this manner, a physician can choose when a procedure warrants using the same flush device that has previously been used for a similar procedure using similar parameters and under the same or similar conditions.

In one embodiment of the invention, means of communication with a base station is embedded and/or associated with the flush device.

In one embodiment of the invention, the communication means utilizes one or more of a wireless local area network; a wireless wide area network; a cellular network; a satellite network; a Wi-Fi network; and a pager network. In one embodiment of the invention, a modem capable of communicating with one or more of the aforementioned networks is embedded in the flush device. In the following discussion the term 'cellular modem' will be used to describe the device embedded. The term 'cellular modem' will be herein used to identify any device of comparable size capable of communicating over one or more of the aforementioned networks. In one embodiment of the invention, the cellular modem can be a Code Division Multiple Access (CDMA) modem. In an embodiment of the invention, a RFID reader and associate integrated circuit processor can be embedded together with the cellular modem in the flush device. In such an embodiment, the RFID tags and RFID reader can be positioned to optimize the RFID read of the RFID tags from the available devices including the filter.

In an embodiment of the invention, a RFID reader and a cellular modem can be positioned in the flush device; the RFID reader is in communication with one or more RFID readers, associated cellular modems and the RFID tags of one or more flush devices including the drainage bag and the filter. Through communications with the RFID reader and associated integrated circuit processor of the plurality of flush devices, a RFID reader and associated integrated circuit processor is able to distinguish the RFID tag from the drainage bag and the filter in the vicinity based on one or more of location, strength of signal, variation of RFID tag signal with position, variation of RFID tag signal with time and prior input data. In an embodiment of the invention, one or more antenna can be used to help discriminate the location of the flush devices including the drainage bag and the filter. In an embodiment of the invention, the RFID reader and associate processor can be in communication with the cellular modem. In an embodiment of the invention, the cellular modem is in communication with a base station and can transmit one or more parameters selected from the group consisting of one or more RFID tag location, one or more RFID tag identification code, flush devices including the drainage bag and the filter, flush device conditions, suction device conditions and time stamp.

In one embodiment of the invention the RFID code uses the IEEE format and is Electronic Product Code (EPC) readable. In another embodiment of the invention the RFID code uses the UCC format and is Universal Product Code (UPC) readable. In another embodiment, the format is compatible for EPC, European Article Number (EAN) and UPC read and write functions.

In an embodiment of the invention, the device method or system can be used for the treatment of humans. In an embodiment of the invention, the device method or system can be used for the treatment of animals. In an embodiment of the invention, the device method or system can be used in veterinary applications. In an embodiment of the invention, the device method or system can be used in medical applications.

In an embodiment of the invention, a flush device including the drainage bag and the filter can be assembled as an integral unit. These components can be attached within or onto integral to the flush device housing. The energy storage device and the pump can also be housed in the integral flush device housing. In an embodiment of the invention, an integral flush device is portable, ergonomic, and superior for in situ use. As the patient moves, the device can move to compensate for the movement. In contrast, if the flush device was separate, or relied upon a tether to hold the device to the patient, then movement could jar and detach the suction device.

In an embodiment of the invention, the flush device further comprises one or both visual and audio feedback that allows one or more methods of control of the back pressure applied to the suction device, control of the flush device and adjustment of the flush device settings during the procedure.

In an embodiment of the invention, the flush device is portable. In an embodiment of the invention, the flush device is hand held. In an embodiment of the invention, the flush device is portable and hand held.

In an embodiment of the invention, a method of adjusting and monitoring a flush device during a procedure, comprises receiving the catheter from the organ and the drainage bag and the filter, applying a back pressure to the filter during the procedure, wherein the flush device one or both receives and has preset parameters to control the back pressure to be applied to the filter. Activating the flush device, wherein the flush device functions include monitoring the back pressure applied to the filter via a sensor, comparing the back pressure applied to the filter and the parameters at regular time intervals using a processor and automatically increasing the flushing of the filter when the comparison indicates an increased back pressure. The method further comprises monitoring the flush device during the procedure using one or both audio or visual feedback from the flush device and adjusting the parameters selected in response to changed conditions of the procedure. In an embodiment of the invention, the back pressure is adjusted to control against build up of material at the filter.

In an embodiment of the invention, the flush device can be applied in any scientific, manufacturing, or industrial apparatus that requires filtered fluid flow and the use of a flush cycle to clear the filter followed by a regulated constant or variable back pressure check to determine that flow through the filter is not impeded. This can include laboratory equipment that requires filtered fluid flow or any other clinical procedure. The manipulation of components, fluids or assemblies used in a manufacturing process, including: precision handling, clean-room transport, and material transport can also be supported.

Various embodiments can be implemented using a conventional general purpose or specialized digital computer(s) and/or processor(s) programmed according to the teachings of the present disclosure, as will be apparent to those skilled in the computer art. Appropriate software coding can readily be prepared by skilled programmers based on the teachings of the present disclosure, as will be apparent to those skilled in the software art. The invention can also be implemented by the preparation of integrated circuits and/or by interconnecting an appropriate network of component circuits, as will be readily apparent to those skilled in the art.

Embodiments of the present invention can include a computer readable medium, such as computer readable storage medium. The computer readable storage medium can have stored instructions which can be used to program a computer to perform any of the features present herein. The storage medium can include, but is not limited to, any type of disk including floppy disks, optical discs, DVD, CD-ROMs, micro drive, and magneto-optical disks, ROMs, RAMs, EPROMs, EEPROMs, DRAMs, flash memory or any media or device suitable for storing instructions and/or data. The present invention can include software for controlling both the hardware of a computer, such as general purpose/specialized computer(s) or microprocessor(s), and for enabling them to interact with a human user or other mechanism utilizing the results of the present invention. Such software may include, but is not limited to, device drivers, operating systems, execution environments/containers, and user applications.

Embodiments of the present invention can include providing code for implementing processes of the present invention. The providing can include providing code to a user in any manner. For example, the providing can include transmitting digital signals containing the code to a user; providing the code on a physical media to a user; or any other method of making the code available.

Embodiments of the present invention can include a computer-implemented method for transmitting the code which can be executed at a computer to perform any of the processes of embodiments of the present invention. The transmitting can include transfer through any portion of a network, such as the Internet; through wires, the atmosphere or space; or any other type of transmission. The transmitting can include initiating a transmission of code; or causing the code to pass into any region or country from another region or country. A transmission to a user can include any transmission received by the user in any region or country, regardless of the location from which the transmission is sent.

In an embodiment of the invention, a flush device comprises a drainage port connectable via a filter to a source of unfiltered fluid, an inlet port in connection with one or both a waste line and a containment bag and a flushing port which can be connected to a fluid reservoir. The flush further comprises a back pressure sensor and a moveable flange for directing the flow from the drainage port to one of the inlet port and the flushing port.

A method of operating a flush device comprises the steps of receiving the flush, connecting a drainage port of the flush with a source of unfiltered serum and connecting an inlet port of the flush with one or both a waste line and a waste container. The method further comprises the steps of connecting a flushing port of the flush to a fluid reservoir containing a fluid and monitoring a back pressure sensor to detect one or both a background back pressure and an increase in the back pressure above the background back pressure. The method further comprises the steps of activating a flange to direct a connection between the drainage port and the inlet port to a connection between the drainage port and the flushing port when the back pressure sensor detects a back pressure greater than the background back pressure and supplying the fluid from the fluid reservoir to the flush. The method of operating the flush where the fluid from the fluid reservoir is supplied to the flush for a specified period of time.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A method of operating a flushing device comprising the steps of:
    (a) receiving the flushing device adapted with a fluid connection between a drainage port and an inlet port when a flange in the flushing device is in a deactivated state, a biasing force urging the flange toward the deactivated state;
    (b) connecting the inlet port of the flushing device with a catheter that is in communication with a source of bodily fluid;
    (c) connecting the drainage port of the flushing device with one or both of a waste line and a waste container so that a passive flow of bodily fluid drains from the source of bodily fluid along a drainage fluid flow path through the catheter and flushing device and to the waste line and/or waste container, a leading edge of the flange being spaced from the drainage fluid flow path when the flange is in the deactivated state;
    (d) connecting a flushing port of the flushing device to a fluid reservoir containing a flushing fluid, the flange remaining in the deactivated state during the step of connecting;
    (e) supplying the flushing fluid from the fluid reservoir through the flushing port against the passive flow of bodily fluid so as to flush the inlet port and the catheter; and
    (f) moving the flange in the flushing device to an activated state so as to place the inlet port into fluid communication with the flushing port, wherein the flange is moved to the activated state by supplying the flushing fluid through the flushing port, the flushing fluid contacting and applying an activation force to the flange sufficient to overcome the biasing force so as to move the flange to the activated state as the flushing fluid is supplied through the flushing port.

2. The method of operating a flushing device of claim 1, where the flushing fluid is supplied for a first specified period of time.

3. The method of operating a flushing device of claim 1, where supplying the flushing fluid is discontinued after the first specified period of time.

4. The method of operating a flushing device of claim 3, wherein when supplying the flushing fluid is stopped, the biasing force automatically moves the flange to the deactivated state, and the fluid connection between the drainage port and the inlet port is reestablished.

5. A method for draining bodily fluid, comprising:
    draining bodily fluid from a patient via a catheter having a first end placed within the patient, a second end of the catheter being attached to a first port of a flushing device, a container being attached to a second port of the flushing device, a drainage fluid flow path defined by a drainage channel formed within the flushing device between the first port and the second port, a passive bodily fluid flow flowing from the patient into the first port, through the flushing device along the drainage fluid flow path and to and through the second port, the flushing device having a flushing fluid input port between the first and second ports, the flushing fluid input port having a valve seat, a plate being biased into a first position in which the plate is received by the valve seat so as to close the flushing fluid input port, a flushing access channel extending from the flushing fluid input port and intersecting the drainage channel;
    applying a force to the plate to overcome the bias and move the plate out of engagement with the valve seat and toward a second position in which the plate blocks the flow path between the first and second ports so that a flushing flow path is established between the flushing fluid input port and the first port, wherein the plate is connected to a hinge positioned on a side of the flushing fluid input port closer to the second port than to the first port, and wherein when the force is applied to the plate, the plate rotates about the hinge;
    infusing a flushing fluid through the flushing fluid input port and along the flushing flow path at sufficient pressure to overcome the passive bodily fluid flow so that that flushing fluid flows along the flushing flow path through the first port and into and through the catheter;
    removing the force from the plate so that the plate automatically moves back into the first position and no longer blocks the flow path between the first and second ports so that the passive bodily fluid flow again flows through the flushing device along the drainage fluid flow path.

6. A method as in claim 5, wherein the force applied to the plate to overcome the bias and move the plate out of engagement with the valve seat is applied by the flushing fluid being infused through the flushing fluid input port.

7. A method as in claim 6, wherein removing the force from the plate comprises stopping infusing flushing fluid through the flushing fluid input port.

8. A method as in claim 6, wherein the second port comprises a second valve seat, and wherein when the plate is in the second position, the plate is engaged with the second valve seat so as to close the second port.

9. A method as in claim 5, wherein the plate is biased into the first position by a spring.

10. A method as in claim 5, additionally comprising a filter upstream of the first input, and wherein when the flushing fluid is being infused, the flushing fluid flows through the filter so as to flush the filter.

11. A method as in claim 5, wherein the flushing access channel intersects the drainage channel at an intersecting section, the drainage fluid flow path extending through the intersecting section, and wherein when the plate is moved toward the second position, the plate moves into the drainage fluid flow path in the intersecting section.

12. A method for draining bodily fluid, comprising:
    draining bodily fluid from a patient via a catheter having a first end placed within the patient, a second end of the catheter being attached to a first port of a flushing device, a container being attached to a second port of the flushing device, a drainage fluid flow path defined by a drainage channel formed within the flushing device between the first port and the second port, a passive bodily fluid flow flowing from the patient into the first port, through the flushing device along the drainage fluid flow path and to and through the second port, the flushing device having a flushing fluid input port between the first and second ports, the flushing fluid input port having a valve seat, a plate being biased into a first position in which the plate is received by the valve seat so as to close the flushing fluid input port, a flushing access channel extending from the flushing fluid input port and intersecting the drainage channel, wherein the plate is disposed within the flushing access channel and spaced from the drainage channel so that the plate is spaced from the drainage fluid flow path when in the first position;

applying a force to the plate to overcome the bias and move the plate out of engagement with the valve seat and toward a second position in which the plate blocks the flow path between the first and second ports so that a flushing flow path is established between the flushing fluid input port and the first port;

infusing a flushing fluid through the flushing fluid input port and along the flushing flow path at sufficient pressure to overcome the passive bodily fluid flow so that that flushing fluid flows along the flushing flow path through the first port and into and through the catheter;

removing the force from the plate so that the plate automatically moves back into the first position and no longer blocks the flow path between the first and second ports so that the passive bodily fluid flow again flows through the flushing device along the drainage fluid flow path.

13. A method as in claim 12, wherein a leading edge of the plate is spaced from the drainage fluid flow path when in the first position.

14. A method as in claim 13, wherein when the plate is moved toward the second position, the leading edge of the plate moves into the drainage fluid flow path.

15. A method as in claim 11, wherein contact of the flushing fluid against the plate during the step of infusing the flushing fluid applies the force to the plate to overcome the bias and move the plate out of engagement with the valve seat.

16. A method as in claim 15 additionally comprising attaching a source of flushing fluid to the flushing fluid input port while the plate remains engaged with the valve seat.

17. A method as in claim 16, wherein the flushing fluid input port is spaced from the drainage channel, and a leading edge of the plate is spaced from the drainage fluid flow path when the plate is in the first position.

18. A method as in claim 17, wherein moving the plate out of engagement with the valve seat and toward the second position comprises rotating the plate about the hinge so that the plate blocks fluid flow from the intersecting section toward the second port.

19. A method as in claim 18, wherein moving the plate out of engagement with the valve seat and toward the second position comprises rotating the plate about the hinge sufficient so that the leading edge of the plate is positioned on a side of the drainage fluid flow path opposite the flushing fluid input port.

* * * * *